United States Patent [19]

Denzler

[11] 4,335,045
[45] Jun. 15, 1982

[54] PREPARATION OF N-ALKENYL-2-AMINOMETHYL-PYRROLIDINES

[75] Inventor: Eric-Alain Denzler, Zurich, Switzerland

[73] Assignee: Sachim S.A., Geneva, Switzerland

[21] Appl. No.: 669,967

[22] Filed: Mar. 24, 1976

[30] Foreign Application Priority Data

Dec. 19, 1975 [CH] Switzerland ............... 16485/75

[51] Int. Cl.$^3$ .......................................... C07D 207/09
[52] U.S. Cl. ................................. 548/566; 564/215; 564/475; 564/510; 548/568
[58] Field of Search ................................. 260/326.85

[56] References Cited

U.S. PATENT DOCUMENTS 3,597,447  8/1971  Kashihara et al. ............ 260/326.85

OTHER PUBLICATIONS

Kirk–Othmer, Encyclopedia of Chemical Technology, (Second Edition, 1969), vol. 19, pp. 397–398.
Mcomie, Advances in Organic Chemistry, Methods and Results, vol. 3, (Interscience Pub., 1963), pp. 206–210.
Wagner et al., Synthetic Organic Chemistry, (New York, 1953), p. 566.

*Primary Examiner*—Alton D. Rollins
*Attorney, Agent, or Firm*—Robert E. Burns; Emmanuel J. Lobato; Bruce L. Adams

[57] ABSTRACT

An N-alkenyl-2-aminomethyl-pyrrolidine is prepared by firstly reacting tetrahydrofurfurylamine with gaseous hydrochloric acid and thionyl chloride to produce 2,5 dichloropentylamine hydrochloride. This is acetylized, possibly by acetyl chloride in dichloroethane in the presence of triethylamine, into N-acetyl-2,5-dichloropentylamine which is condensed with an alkenylamine into an N-alkenyl-2-acetylaminomethyl pyrrolidine from which the acetyl group is separated, for example by boiling with concentrated hydrochloric acid.

4 Claims, No Drawings

PREPARATION OF N-ALKENYL-2-AMINOMETHYL-PYRROLIDINES

The invention concerns the preparation of N-alkenyl-2-aminomethyl-pyrrolidines, in particular N-allyl-2-aminomethylpyrrolidine.

The use of N-substituted 2-aminomethyl-pyrrolidines is known for the preparation of pharmaceutically-valuable benzamides which are used as medicaments in the fields of gastro-enterology and neurology. It is however known that it is not possible, in a secondary chain of the nitrogen atom in the pyrrolidine ring, to prepare non-saturated alkenyl derivatives by treating a nitromethylene group in the α-C atom of the pyrrolidine ring by nascent hydrogen, or by catalytic hydrogenation (W. German published patent applications (DOS) Nos. 1,941,536; 1,966,195 and 2,152,371) since this would also produce hydrogenation of a non-saturated double linking in the secondary N-chain.

For the purpose of avoiding this undesirable hydrogenation in the non-saturated double linkings in a secondary N chain when hydrogen is used for reduction of the nitromethylene group, it is known to use a selective reduction by means of lithium aluminium hydride (Li Al H$_4$) (W. German Published Patent Application (DOS) No. 2,216,738), whereby the unsaturated double linkings in the secondary N chain are not acted upon, and there is solely a reduction of the nitromethylene group on the α-C atom of the pyrrolidine ring of the aminomethyl group.

It has now been discovered that to the contrary it is possible to avoid hydrogenation and, above all, a reduction of the α-nitromethylene group in the presence of sensitive non-saturated double linkings in the secondary N-chain, starting from an initial substance already containing the aminomethyl group, and by introducing the secondary alkenyl chain into this molecule.

According to the invention, a process of preparing an N-alkenyl-2-aminomethyl pyrrolidine comprises reacting tetrahydrofurfurylamine with gaseous hydrochloric acid and thionyl chloride whereby by opening the ring 2,5-dichloropentylamine hydrochloride is obtained; this is then acetylized into N-acetyl-2,5-dichloropentylamine which is condensed by an alkenylamine into an N-alkenyl-2-acetylaminomethyl-pyrrolidine ring from which the acetyl group is separated.

This process may take place according to the following reaction scheme:

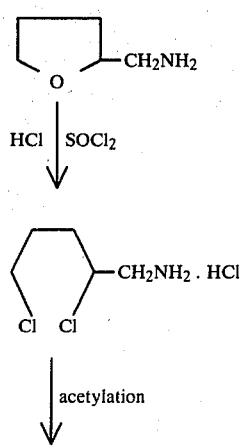

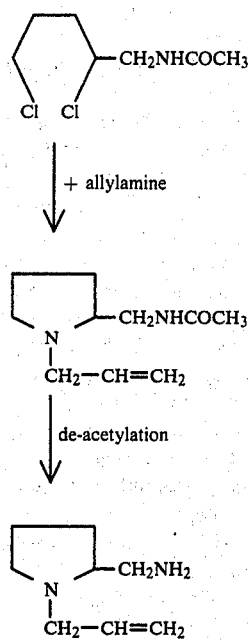

Acetylation of the 2,5-dichloropentylamine can take place in a simple and suitable manner by means of acetyl chloride in dichloroethane in the presence of triethylamine or by means of anhydrous acetic acid. After reclosing the ring, the acetyl group can be separated in an acid or an alkaline medium.

The technical and economic advantages of this process reside principally in that it is possible to avoid the use of the relatively expensive lithium-aluminium hydride which is difficult to use at the low temperatures necessary to avoid undesirable secondary reactions due to its reactivity, and in that despite a supplementary operation there is about the same qualitative and quantitative yield.

The practical application of the process according to the invention will be explained by an example of the preparation of N-allyl-2-aminomethyl-pyrrolidine:

(a) Preparation of 2,5 dichloropentylamine-hydrochloride (M=192.5).

In a 5-liter flask provided with a mechanical stirrer, a cooler connected to a gas washing bottle filled with sulphuric acid and to a gas-delivery tube, are placed 202 g (2 Mol) of tetrahydrofurfurylamine.

A stream of gaseous hydrochloric acid is delivered by the gas delivery tube. The reaction is very exothermic and the temperature rapidly reaches 100°–110° C. This temperature is maintained by cooling the flask and by adjusting the supply of gaseous hydrochloric acid. After about four hours, the gaseous hydrochloric acid is no longer absorbed.

The reaction mixture is cooled to 55°–60° C. and one liter of chloroform is added. The gas delivery tube is replaced by a dropping funnel in which 350 ml of freshly distilled thionyl chloride is introduced. The thionyl chloride is allowed to drop slowly, and the reaction mixture progressively dissolves. Reflux heating is continued for two hours, and an abundant precipitate appears. The reaction mixture is allowed to cool and stand overnight. The precipitate formed is filtered, washed with chloroform and the product obtained dried in a drying chamber.

There is hence obtained 306 g (approx. 80%) of 2,5-dichloropentylamine hydrochloride with a melting point of 160° C.

(b) Preparation of N-acetyl-2,5-dichloropentylamine (M=198).

In a 3-liter flask with a stirrer, a cooler, a thermometer and a dropping funnel is placed 193 g (=1 Mol) of 2,5-dichloropentylamine hydrochloride, 300 g of triethylamine and 850 ml of dichloroethane. While the mixture is stirred, 100 g of acetyl chloride dissolved in 400 ml of dichloroethane is slowly dropped in by means of the dropping funnel. The temperature is maintained at 25° C. by cooling the flask with a cooling mixture. Stirring is continued for two hours after the introduction of the acetyl chloride. The triethylamine hydrochloride formed is then filtered and washed with dichloroethane. The filtrate is washed with water and the organic solution dried and evaporated under vacuum. The residue is recrystallized in toluene, filtered, and dried in a drying chamber.

There is obtained 172 g (approx. 87%) of N-acetyl-2,5-dichloropentylamine.

(c) Preparation of N-allyl-2-acetylaminomethyl-pyrrolidine (M=182).

In a two-liter flask with a stirrer and a thermometer, is introduced 160 g (=0.8 Mol) of N-acetyl-2,5-dichloropentylamine and 182 g of allylamine. The reaction mixture is stirred until it dissolves, and allowed to stand for two days at normal room temperature, then heated between 60° and 65° for seven hours. After cooling, a solution of 110 g of potassium carbonate in 300 ml of methanol is slowly added, while cooling. The potassium chloride obtained is filtered off. The filtrate is evaporated to dryness and the residue taken up in ether. The distilled ether leaves an oily product which is distilled under vacuum and then crystallises rapidly.

There is obtained 101 g (approx. 69%) of N-allyl-2-acetylaminomethyl-pyrrolidine with a melting point of 42° C.

(d) Preparation of N-allyl-aminomethyl-pyrrolidine (M=140).

In a 2-liter flask with a thermometer, stirrer, cooler, and a dropping funnel is placed 350 ml of concentrated hydrochloric acid, and 182 g (1 Mol) of N-allyl-2-acetylaminomethyl-pyrrolidine is slowly added while cooling. This is reflux heated for four hours, cooled filtered and the filtrate alkalised with caustic soda. The suspension obtained is then extracted four times with 200 ml of methylene chloride. The solution is distilled and the residue rectified.

There is obtained 95 g (approx. 68%) of N-allyl-2-aminomethyl-pyrrolidine with a boiling point at 40 mm of Hg of 98°–99° C. and an $n_D20$ value of 1.4779.

What is claimed is:

1. A process of preparing an N-alkenyl-2-aminomethyl-pyrrolidine comprising the steps of
    (a) reacting tetrahydrofurfurylamine with gaseous hydrochloric acid and thionyl chloride at temperatures up to 110° C. to produce 2,5 dichloropentylamine hydrochloride,
    (b) acetylizing the 2,5 dichloropentylamine hydrochloride with acetyl chloride to form N-acetyl-2,5-dichloropentylamine,
    (c) condensing the N-acetyl-2,5-dichloropentylamine with an alkenylamine to form an N-alkenyl-2-acetylaminomethyl pyrrolidine,
    (d) then removing the acetyl group from the N-alkenyl-2-acetylaminomethyl pyrrolidine by acidifying, and then
    (e) alkalizing the product of step (d),
    (f) and recovering said N-alkenyl-2-aminomethyl-pyrrolidine.

2. A process according to claim 1, in which the 2,5-dichloropentylamine hydrochloride is acetylized by acetyl chloride in dichloroethane in the presence of triethylamine.

3. A process according to claim 1, in which the alkenylamine is allylamine.

4. A process according to claim 1, in which the acetyl group is separated by boiling the N-alkenyl-2-acetylaminomethyl pyrrolidine with concentrated hydrochloric acid, and then the resulting product is alkalized by caustic soda.

* * * * *